(12) United States Patent
Iida (10) Patent No.: US 8,221,309 B2
(45) Date of Patent: Jul. 17, 2012

(54) ENDOSCOPE PROCESSOR

(75) Inventor: Mitsuru Iida, Saitama (JP)

(73) Assignee: Hoya Corporation, Tokyo (JP)

( * ) Notice: Subject to any disclaimer, the term of this patent is extended or adjusted under 35 U.S.C. 154(b) by 1275 days.

(21) Appl. No.: 11/874,456

(22) Filed: Oct. 18, 2007

(65) Prior Publication Data

US 2008/0255415 A1 Oct. 16, 2008

(30) Foreign Application Priority Data

Oct. 19, 2006 (JP) ................................ 2006-285052

(51) Int. Cl.
*A61B 1/00* (2006.01)
*A61B 1/04* (2006.01)

(52) U.S. Cl. ...................................................... 600/118

(58) Field of Classification Search .................. 600/101, 600/109, 118, 152, 159, 180
See application file for complete search history.

(56) References Cited

U.S. PATENT DOCUMENTS

| | | | | |
|---|---|---|---|---|
| 6,120,435 | A * | 9/2000 | Eino | 600/118 |
| 6,322,496 | B1 | 11/2001 | Iida et al. | |
| 6,491,628 | B1 | 12/2002 | Kobayashi | |
| 6,980,227 | B2 | 12/2005 | Iida et al. | |
| 7,218,340 | B2 | 5/2007 | Takahashi et al. | |
| 2004/0024288 | A1 * | 2/2004 | Uchikubo | 600/101 |
| 2005/0049456 | A1 | 3/2005 | Iida | |
| 2005/0215857 | A1 * | 9/2005 | Iwasaki | 600/118 |
| 2005/0256370 | A1 * | 11/2005 | Fujita | 600/101 |
| 2006/0015012 | A1 * | 1/2006 | Sato | 600/118 |
| 2007/0066866 | A1 * | 3/2007 | Noguchi et al. | 600/102 |
| 2008/0015415 | A1 * | 1/2008 | Obata et al. | 600/118 |

FOREIGN PATENT DOCUMENTS

| | | |
|---|---|---|
| JP | 8-123518 | 5/1996 |
| JP | 8-331293 | 12/1996 |
| JP | 2000-139834 | 5/2000 |
| JP | 2001-137183 | 5/2001 |
| JP | 2001-235686 | 8/2001 |
| JP | 2002-248099 | 9/2002 |
| JP | 2005-329130 | 12/2005 |
| JP | 2006-122125 | 5/2006 |

OTHER PUBLICATIONS

English language Abstract of JP 2001-137183.
English language Abstract of JP 2005-329130.
Japan Office action, dated Oct. 25, 2011 along with an english translation thereof.

\* cited by examiner

*Primary Examiner* — Philip R Smith
(74) *Attorney, Agent, or Firm* — Greenblum & Bernstein, P.L.C.

(57) ABSTRACT

An endoscope processor comprising a touch-panel input unit, a mechanical switch unit, and a controller, is provided. The endoscope processor controls an endoscope system. The touch-panel input unit comprises a touch-panel monitor. A command to carry out a function of the endoscope system is input via a command-input display displayed on the touch-panel monitor. The mechanical switch unit is manipulated to carry out at least one function among a light-switching function, a pump-switching function, and a white-balance-start switching function. The controller carries out a function corresponding to the command input via the touch-panel input unit or the mechanical switch unit.

2 Claims, 7 Drawing Sheets

ENDOSCOPE PROCESSOR

BACKGROUND OF THE INVENTION

1. Field of the Invention

The present invention relates to an endoscope processor having a touch-panel input unit into which a user inputs an operational command to perform some functions of an endoscope system.

2. Description of the Related Art

Recent endoscope systems have various functions. Many buttons are necessary to permit command input to carry out each of the functions. In order to decrease the number of buttons, Japanese Patent Publication No. 2005-329130 discloses an endoscope processor comprising a touch-panel input unit.

In general, a CPU, in which a driver program is installed, drives the touch-panel monitor which the touch-panel input unit comprises. However, if it is the CPU that drives the touch-panel monitor, it may take a while to start the driver program. Consequently, the user faces a problematic delay in being able to manipulate the endoscope system after switching it on.

SUMMARY OF THE INVENTION

Therefore, an object of the present invention is to provide an endoscope processor that has a touch-panel input unit and enables the user to observe a desired subject, quickly after switching on the endoscope system.

According to the present invention, an endoscope processor comprising a touch-panel input unit, a mechanical switch unit, and a controller, is provided. The endoscope processor controls an endoscope system. The endoscope system comprises an electronic endoscope and the endoscope processor. The endoscope is used for observing a subject. The touch-panel input unit comprises a touch-panel monitor. A command to carry out a function of the endoscope system is input via a command-input display displayed on the touch-panel monitor. The mechanical switch unit is manipulated to carry out at least one function among a light-switching function, a pump-switching function, and a white-balance-start switching function. By the light-switching function, a light source to illuminate the subject is switched on or off. By the pump-switching function, a pump for sending a fluid to peripheral area of the subject starts or stops. Upon activation of the white-balance-start switching function, a white balance adjustment of the electronic endoscope starts. The controller carries out a function corresponding to the command input via the touch-panel input unit or the mechanical switch unit.

Further, the controller comprises a first and a second control blocks. The first control block carries out the function corresponding to the command input on the mechanical switch unit. The second control block carries out the function corresponding to the command input on the touch-panel input unit.

Further, the controller comprises a first and a second control blocks. The first control block carries out the function corresponding to the command input on the mechanical switch unit. The second control block drives the touch-panel input unit and communicates the command input on the touch-panel input unit to the first control block. The first control block carries out the function corresponding to the command input on the touch-panel input unit when the command input on the touch-panel input unit is communicated to the first control block.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

The present invention is described below with reference to first and second embodiments shown in the drawings.

Figure 1:
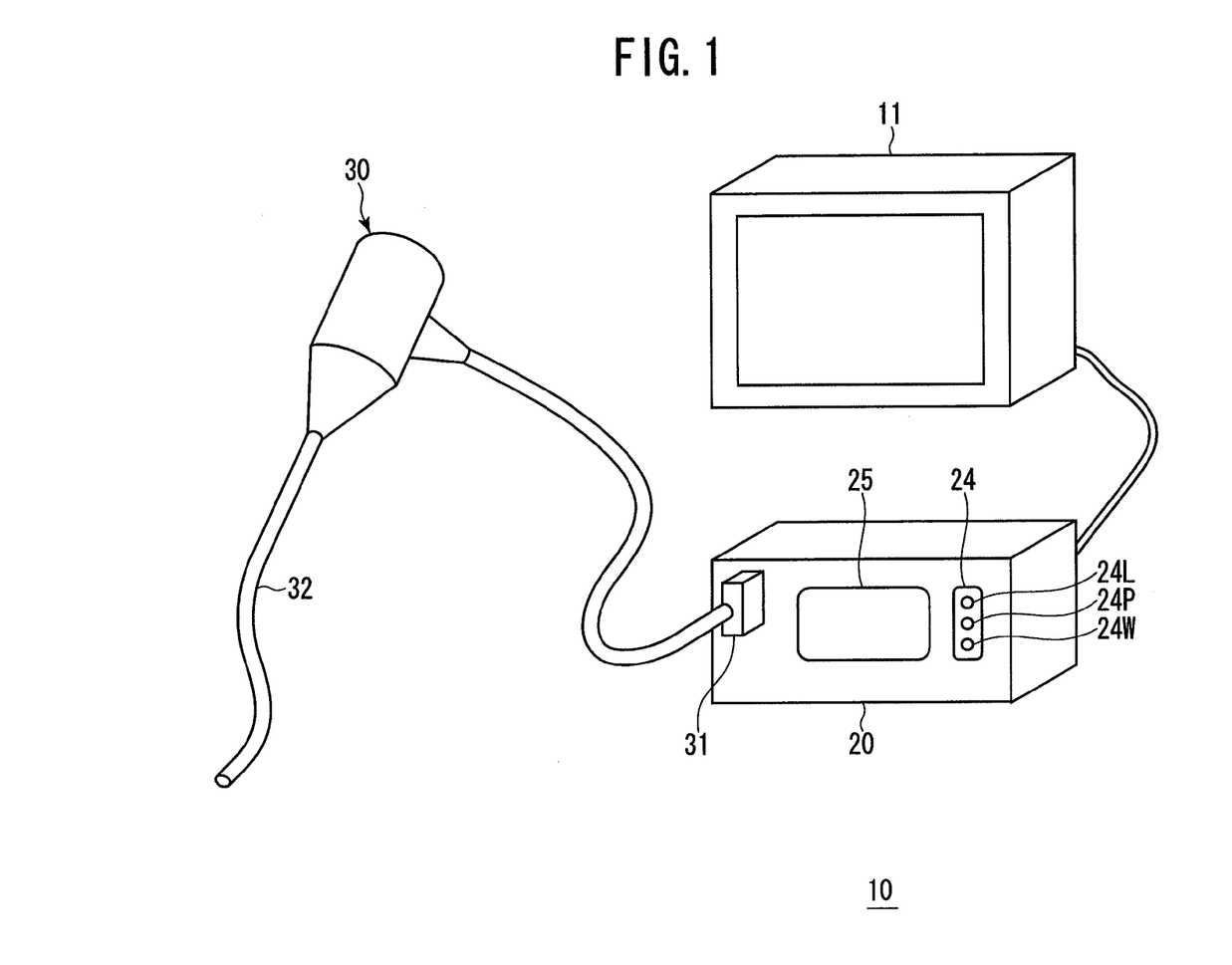
FIG. 1 is a perspective view of an endoscope system having an endoscope processor as a first embodiment of the present invention.

In FIG. 1, an endoscope system 10 of a first embodiment comprises an endoscope processor 20, an electronic endoscope 30, and a monitor 11. The electronic endoscope 30 is connected to the endoscope processor 20 via the connector 31. The monitor 11 is connected to the endoscope processor 20 via a connector (not depicted).

The whole structure of the endoscope system 10 is briefly explained. A light-source unit (not depicted in FIG. 1) which is housed in the endoscope processor 20 supplies light to the electronic endoscope 30. The supplied light is transmitted to the head end of an insertion tube 32 and illuminates a peripheral area around the head end of the insertion tube 32 of the electronic endoscope 30. An optical image of the illuminated subject is captured by the imaging device (not depicted in FIG. 1), such as a CCD image sensor, mounted at the head end of the insertion tube 32.

Subsequently, an image signal corresponding to the image of the captured subject is generated by the imaging device. The image signal is sent to the endoscope processor 20, where predetermined signal processing is carried out on the image signal. The image signal, having undergone the predetermined signal processing, is sent to the monitor where the resulting image is displayed.

Figure 2:
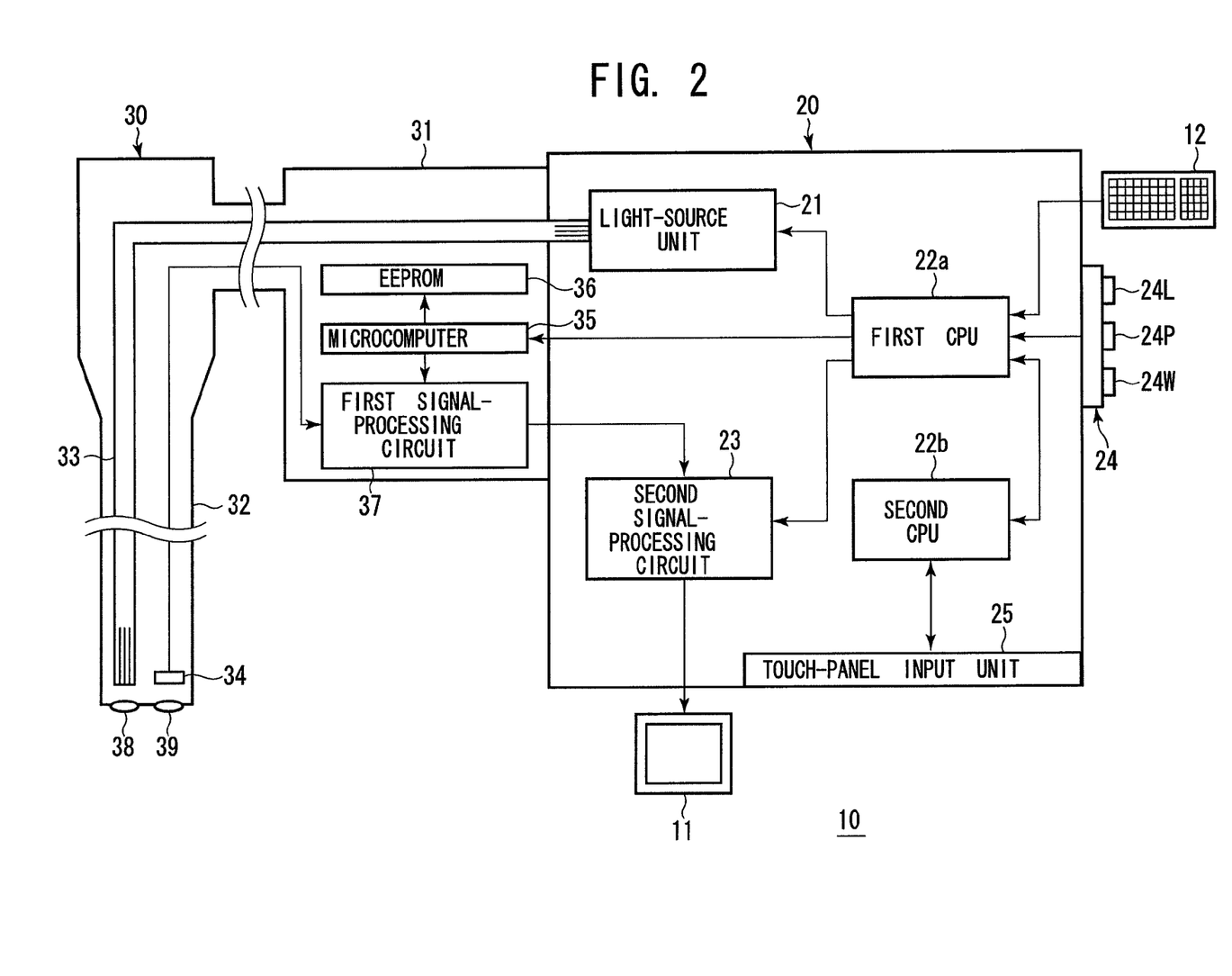
FIG. 2 is a block diagram showing the internal structure of the electronic endoscope and the endoscope processor of the first embodiment.

Next, an internal mechanism of the electronic endoscope 30 and the endoscope processor 20 is explained in detail with reference to FIG. 2.

The electronic endoscope 30 comprises a light guide 33, the imaging device 34, a microcomputer 35, an electrically erasable programmable ROM (EEPROM) 36, a first signal-processing circuit 37, and other components.

The light guide 33 is a bundle of optical fibers, of which one end, hereinafter referred to as an incident end, is mounted in the connector 31 and the other end, hereinafter referred to as an exit end, is mounted in the head end of the insertion tube 32. Illumination light incident on the incident end is transmitted to the exit end. The illumination light transmitted to the exit end illuminates a peripheral area around the head end of the insertion tube 32 after passing through a diffuser lens 38.

An optical image of the illuminated subject is focused onto the light-receiving surface of the imaging device 34 by an object lens 39. The imaging device 34 generates an image signal corresponding to the optical image focused onto the light-receiving surface. The image signal is sent to the first signal-processing circuit 37 housed in the connector 31.

The first signal-processing circuit 37 carries out predetermined signal processing on the received image signal, such as white-balance processing, and black-balance processing. The image signal, having undergone predetermined signal processing, is sent to the endoscope processor 20. The microcomputer 35 controls some components of the electronic endoscope 30 in order to carry out some operations such as the predetermined signal processing carried out by the first signal-processing circuit 37, and the release operation by the imaging device 34. Necessary data for the control of the microcomputer 35 is stored in the EEPROM 36.

The endoscope processor 20 comprises the light-source unit 21, first and second CPUs 22a and 22b, a second signal-processing circuit 23, a mechanical switch unit 24, a touch-panel input unit 25, and other components.

When the electronic endoscope 30 is connected to the endoscope processor 20, the light guide 33 is optically connected to the light-source unit 21. When the user observes a subject with the electronic endoscope 30, light emitted by the light-source unit 21 is supplied to the incident end of the light guide 33 as illumination light.

In addition, when the electronic endoscope 30 is connected to the endoscope processor 20, the first and second signal-processing circuits 37 and 23 communicate electronically with each other. The image signal output from the first signal-processing circuit 37 is input to the second signal-processing circuit 23. The second signal-processing circuit 23 carries out predetermined signal processing on the received image signal. The image signal, having undergone predetermined signal processing, is sent to the monitor 11, as described above.

The first CPU 22a controls the operation of the light-source unit 21, the second signal-processing circuit 23, and each component of the endoscope system 10. The first CPU 22a controls those components according to the user's command input to a keyboard 12, the mechanical switch unit 24, or the touch-panel input unit 25.

The mechanical switch unit 24 is mounted on the front of the endoscope processor 20 (see FIG. 1). The mechanical switch unit 24 has a lamp switch 24L, a pump switch 24P, and a white-balance switch 24W.

By operating the lamp switch 24L, a light-switching function is carried out. The light-switching function switches the light-source unit 21. By operating the pump switch 24P, a pump-switching function is carried out. The pump-switching function starts or stops a pump (not depicted) which sends air or water to the head end of the insertion tube 32 via an air channel (not depicted) of the electric endoscope 30. By operating the white-balance switch 24W, a white-balance-start switching function is carried out. On activation of the white-balance-start switching function, a coefficient for white balance is calculated.

The touch-panel input unit 25 is mounted on the front of the endoscope processor 20 (see FIG. 1). The touch-panel input unit comprises an LCD (touch-panel monitor not depicted). A location touched on the LCD can be detected. Various kinds of command-input displays are displayed on the LCD.

Each of the command-input displays includes some function button icons. There are various predetermined function button icons, such as a luminosity-adjustment button icon, a color-balance button icon, a menu-button icon, a lamp-button icon, a pump-button icon, and a white-balance button icon. When a user touches one function button icon, the endoscope system 10 carries out the function corresponding to the touched function button icon. For example, a basic command-input display is displayed on observation of a subject, and includes the luminosity-adjustment button icon used for adjusting the luminosity of the monitor 11, the color-balance button icon used for adjusting the color balance of an image displayed on the monitor 11, and the menu-button icon used for changing the currently displayed command-input display to a different command-input display. In addition, the basic command-input display includes the lamp-button icon, the pump-button icon, and the white-balance button icon corresponding to the lamp switch 24L, the pump switch 24P, and the white-balance switch 24W mounted in the mechanical switch unit 24, respectively.

The touch-panel input unit 25 detects the user's command input through the function button icons, when the user touches them. In addition, the touch-panel input unit 25 is driven by the second CPU 22b. The second CPU 22b changes to display a command-input display and detects which function button icon has been touched based on the touched location and the currently displayed command-input display, then generates a command-input signal corresponding to the touched function button icon, and sends the command-input signal to the first CPU 22a.

Figure 3:
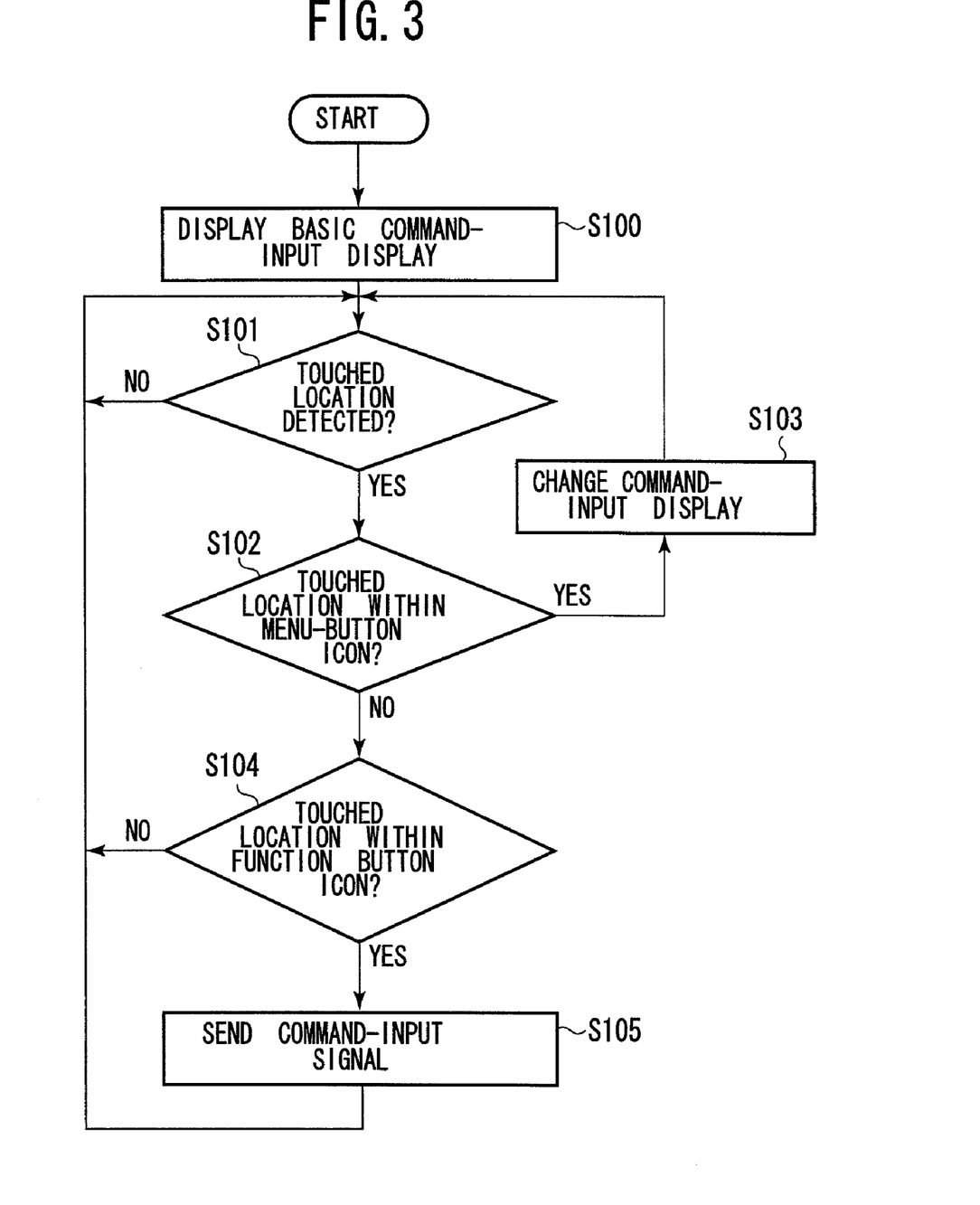
FIG. 3 is a flowchart describing the process for driving the touch-panel input unit as carried out by a second CPU in the first embodiment.
Figure 4:
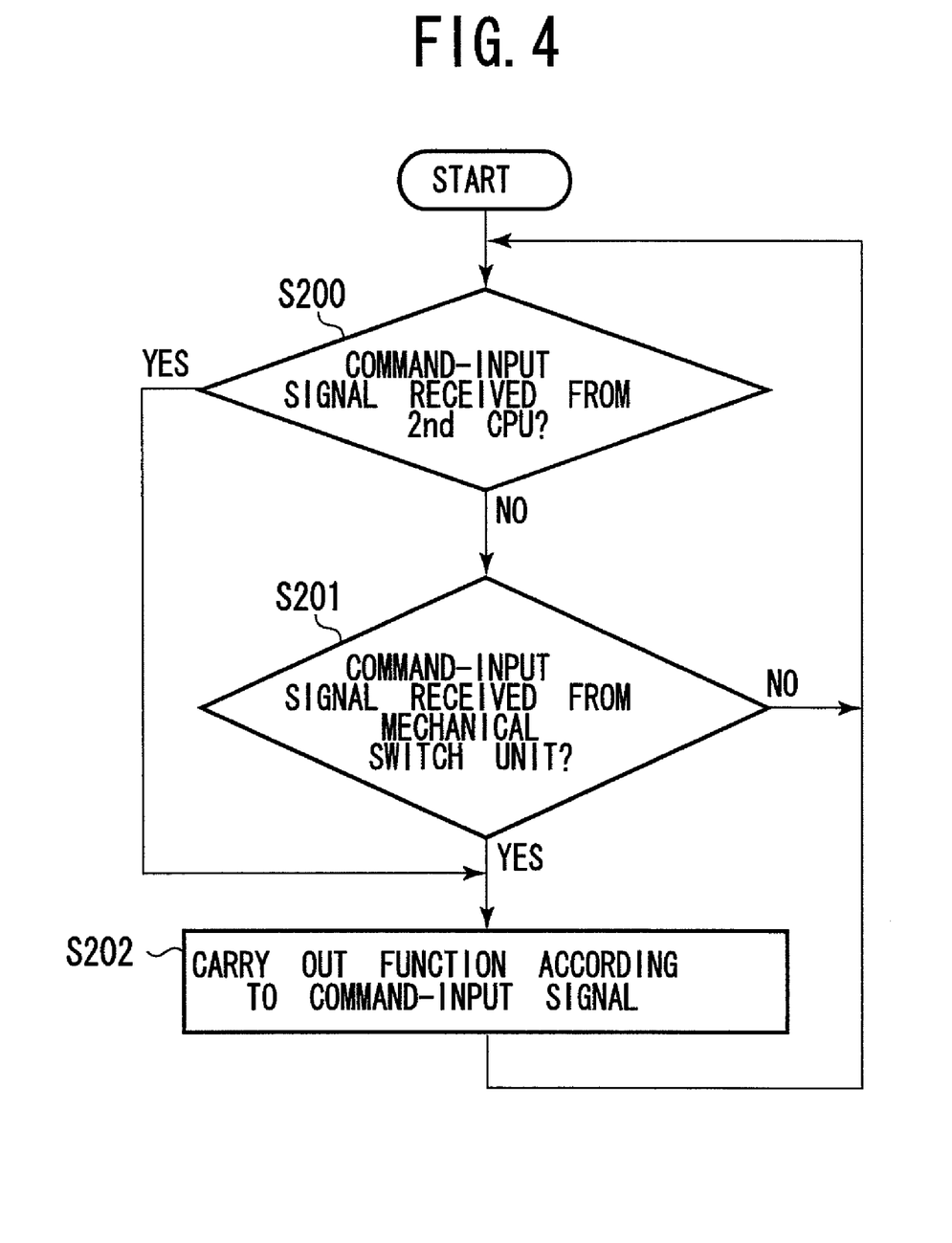
FIG. 4 is a flowchart describing the process for controlling each component of the endoscope system with the first CPU in the first embodiment.

Next, the processing which the second CPU 22b performs to drive the touch-panel input unit 25 and the processing which the first CPU 22a performs to control some components of the endoscope system 10, are explained below, using the flowcharts of FIGS. 3 and 4. The processing carried out by the first and the second CPUs 22a and 22b starts when the endoscope processor 20 is switched on. In addition, the processing ends when the endoscope processor 20 is switched off.

At step S100, a basic command-input display is displayed on the LCD of the touch-panel input unit 25. At step S101, it is determined whether a touch on the LCD has been detected. If a touch is not detected, meaning that the user has not touched the LCD, step S101 is repeated. When a touch and its location are detected, the process proceeds to step S102.

At step S102, it is determined whether the touched location is on the menu-button icon. When the touched location is on the menu-button icon, the process proceeds to step S103, where a command-input display assigned to the touched menu-button icon is displayed on the LCD of the touch-panel input unit 25, and then the process returns to step S101.

When the touched location is not on a menu-button icon at step S102, the process proceeds to step S104. At step S104, it is determined whether the touched location matches a function button icon other than the menu-button icon.

When the touched location does match the function button icon, the process proceeds to step S105, where the command-input signal corresponding to the touched function button icon is generated and sent to the first CPU 22a. After sending the command-input signal or when the touched location does not match the function button icon at step S104, the process returns to step S101.

At step S200, the first CPU 22a determines whether the second CPU 22b has sent a command-input signal. When the first CPU 22a receives the command-input signal from the second CPU 22b, the process skips step S201 and proceeds to step S202. On the other hand, when the CPU 22a does not receive the command-input signal from the second CPU 22b, the process proceeds to step S201.

At step S201, the first CPU 22a determines whether the mechanical switch unit 24 has sent a command-input signal. If the first CPU 22a does not receive a command-input signal from the mechanical switch unit 24, the process returns to step S200. On the other hand, when the first CPU 22a receives a command-input signal from the mechanical switch unit 24, the process proceeds to step S202.

At step S202, the first CPU 22a orders component of the endoscope system 10 to carry out the function corresponding to the command-input signal received at step S200 or S201. After carrying out the function, the process returns to step S200.

In the first embodiment above, the basic functions necessary for observing a subject with an endoscope processor can be carried out by a command input to the mechanical switch unit 24 via the first CPU 22a. Accordingly, the user is more quickly able to manipulate the endoscope processor 20 to observe a desired subject more quickly after switching on the endoscope system 10 because such observation functions can be carried out without waiting for the start-up of the driver program for the touch-panel input unit 25.

Furthermore, even if the touch-panel input unit 25 malfunctions, the user may at least continue observing a subject.

Figure 5:
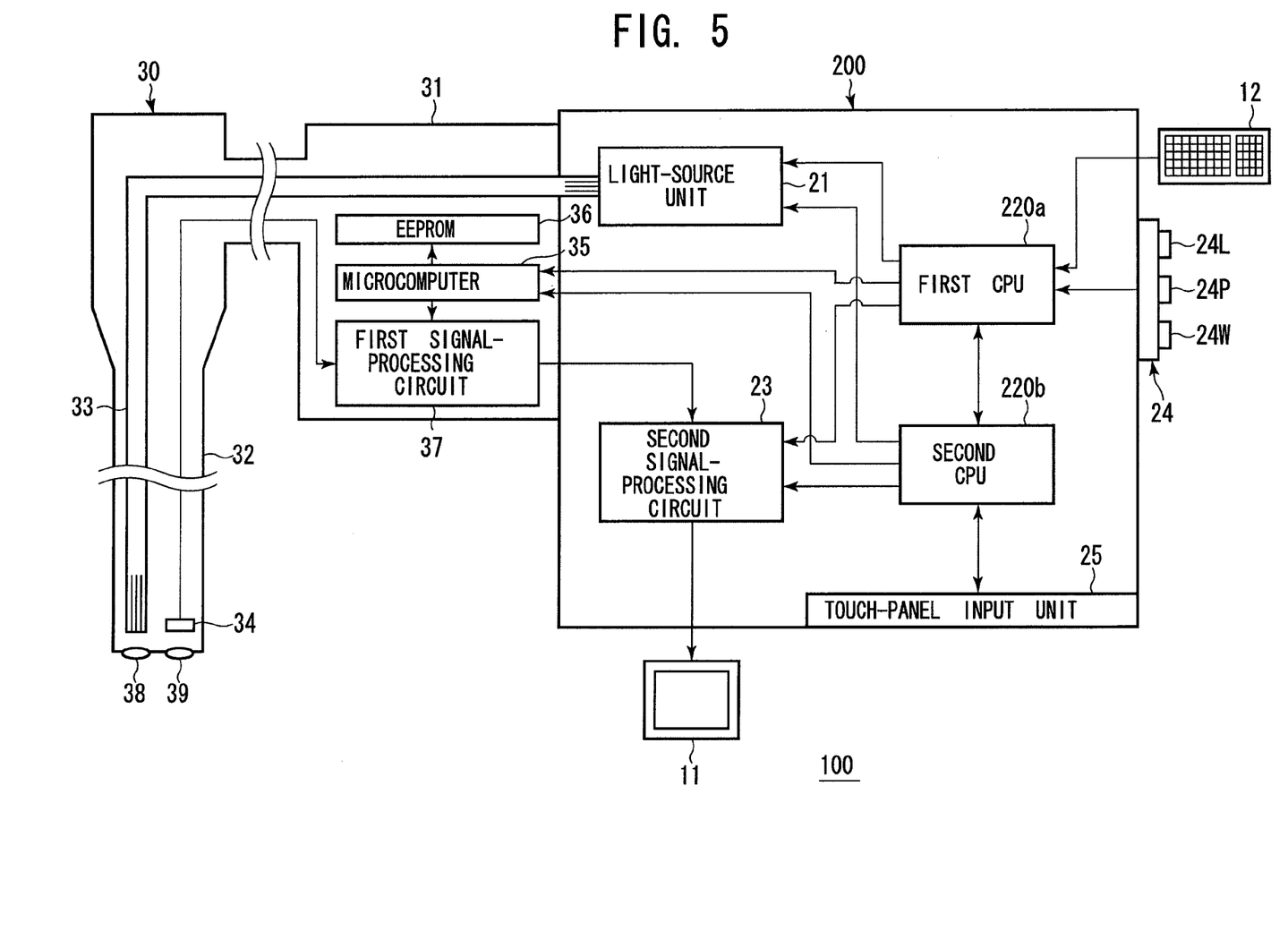
FIG. 5 is a block diagram showing the internal structure of the electronic endoscope and the endoscope processor of the second embodiment.

Next, the endoscope processor of the second embodiment is explained below with reference to FIG. 5. The primary difference between the second embodiment and the first embodiment, which is explained below, is a structure that enables the second CPU to directly control the operation of some components of the endoscope system. Here, the same index numbers are used for the structures that correspond to those of the first embodiment.

The endoscope processor 200 comprises a light-source unit 21, first and second CPUs 220a and 220b, a second signal-processing circuit 23, a mechanical switch unit 24, a touch-panel input unit 25, and other components, as in the first embodiment.

When the electronic endoscope 30 is connected to the endoscope processor 200, the light guide 33 is optically connected to the light-source unit 21, and the first and second signal-processing circuits 37 and 23 communicate electronically with each other, as in the first embodiment. In addition, the light-source unit 21 emits light for illuminating a subject, then an image signal representing the optical image of the illuminated subject is generated, the image signal sent to the second signal-processing circuit 23 undergoes predetermined signal processing, and finally the image signal is sent to the monitor 11, as in the first embodiment.

The first CPU 220a controls the operation of the light-source unit 21, the second signal-processing circuit 23, and some components of the endoscope system 100, as in the first embodiment.

Unlike in the first embodiment, the second CPU 220b can also control each component of the endoscope system 100 according to a command input via the touch-panel input unit 25. However, the operation carried out by the second CPU 220b is communicated to the first CPU 220a because the first CPU 220a is the primary controller for all operations of the endoscope system 100.

In addition, the structures and functions of the keyboard 12, the mechanical switch unit 24, and the touch-panel input unit 25 are the same as those of the first embodiment.

The second CPU 220b drives the touch-panel input unit 24, and detects which function button icon has been touched based on the touched location on the LCD and the currently displayed command-input display, as in the first embodiment.

However, unlike in the first embodiment, the second CPU 220b carries out the function instructed by the command input via a given function button icon, and informs the first CPU 220a of each operation carried out to serve that function.

Figure 6:
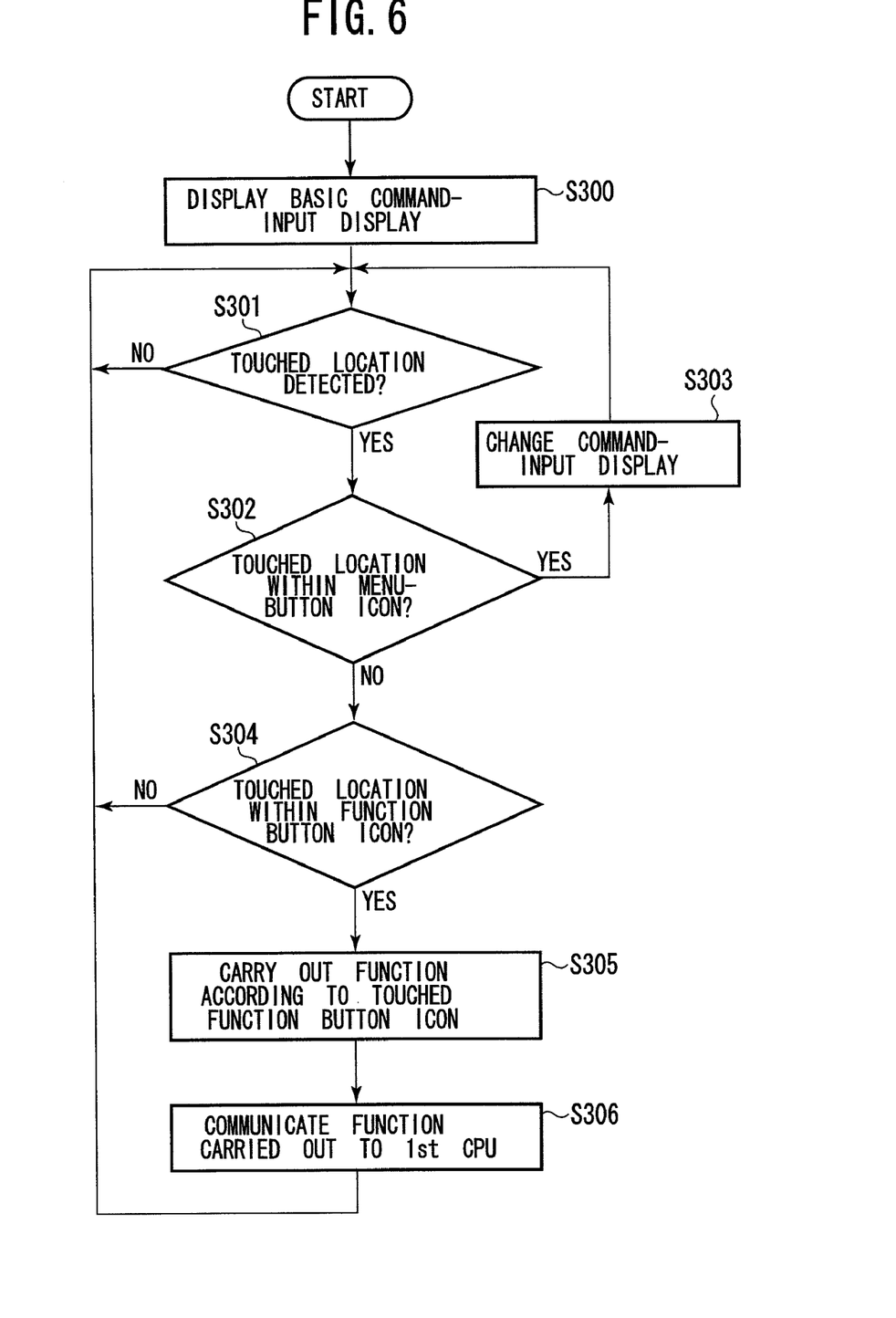
FIG. 6 is a flowchart describing the process for controlling each component of the endoscope system with the second CPU in the second embodiment.
Figure 7:
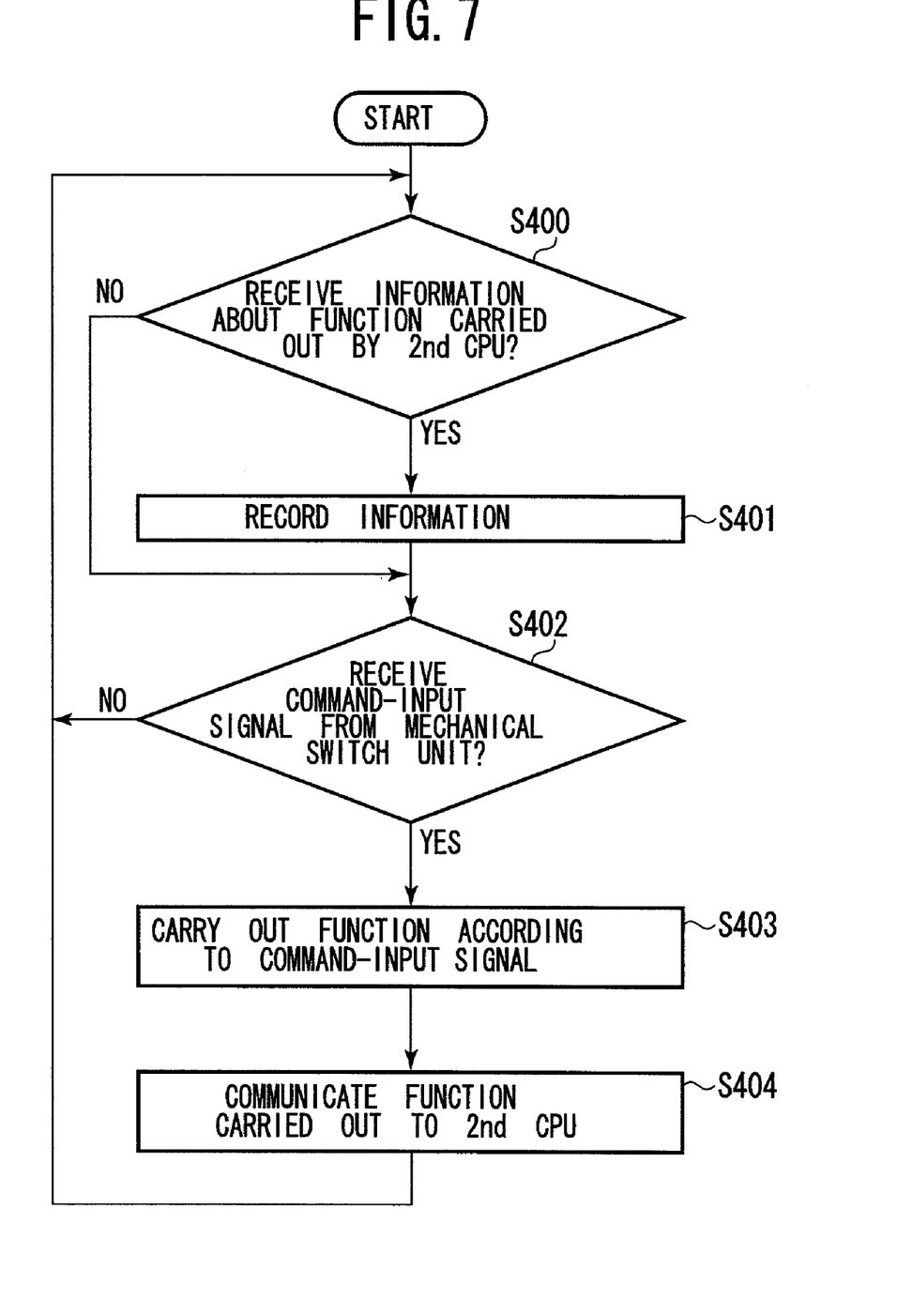
FIG. 7 is a flowchart describing the process for controlling each component of the endoscope system with the first CPU in the second embodiment.

Next, the processing which the second CPU 220b carries out to control some components of the endoscope system 100, and the processing which the first CPU 220a performs to control some components of the endoscope system 100 is explained below, using the flowcharts of FIGS. 6 and 7. The processing carried out by the first and second CPUs 220a and 220b starts when the endoscope processor 200 is switched on. In addition, the processing ends when the endoscope processor 200 is switched off.

At step S300, a basic command-input display is displayed on the LCD of the touch-panel input unit 25. At step S301, it is determined whether a touch on the LCD has been detected. If a touch is not detected, meaning that the user has not touched the LCD, step S301 is repeated. When a touch and its location have been detected, the process proceeds to step S302.

At step S302, it is determined whether the touched location matches the menu-button icon. When the touched location matches the menu-button icon, the process proceeds to step S303, where a command-input display corresponding to the touched menu-button icon is displayed on the LCD of the touch-panel input unit 25, and then the process returns to step S301.

When the touched location does not match the menu-button icon at step S302, the process proceeds to step S304. At step S304, it is determined whether the touched location matches the function button icons.

When the touched location does not match the function button icons, the process returns to step S301. When the touched location does match the function button icons, the process proceeds to step S305, where the second CPU 220b orders each component of the endoscope system 100 to carry out the function corresponding to the command input via the touched function button icon. After performing the function, the process proceeds to step S306. At step S306, the operations required for the function performed by the second CPU 220b are communicated to the first CPU 220b, and then the process returns to step S301.

At step S400, the first CPU 220a determines whether an operation carried out by the second CPU 220b has been communicated to the first CPU 220a. If no operation has been communicated to the first CPU 220a, the process skips step S401 and proceeds to step S402. If an operation has been communicated to the first CPU 220a, the process proceeds to step S401.

At step S401, the communicated operation is recorded in RAM (not depicted) connected to the first CPU 220a. The communicated operation is used for the first CPU 220a to control the whole of the endoscope system 100. After recording, the process proceeds to step S402.

At step S402, the first CPU 220a determines whether the mechanical switch unit 24 has sent a command-input signal. If the first CPU 220a has not received a command-input signal from the mechanical switch unit 24, the process returns to step S400. On the other hand, when the first CPU 220a has received the command-input signal from the mechanical switch unit 24, the process proceeds to step S403.

At step S403, the first CPU 220a orders component of the endoscope system 100 to carry out the functions ordered by the command-input signal received at step S402. After carrying out the function, the process proceeds to step S404, where the function carried out by the first CPU 220a is communicated to the second CPU 220b. After communication, the process returns to step S400.

In the above second embodiment, the minimum functions required for observation of a subject by an endoscope processor can be carried out by operating to the mechanical switch unit 24. Thus, the user is more quickly able to manipulate the endoscope processor 200 for observation of a desired subject after switching on the endoscope system 100, as in the first embodiment.

In addition, as for the second embodiment, a function ordered by a command input to the touch-panel input unit 25 can be carried out by the second CPU 220b, independent of the first CPU 220a. Consequently, even if the CPU 220a malfunctions, the user may continue observing a subject.

In the above first and second embodiments, the basic command-input display includes a lamp-button icon, a pump-button icon, and a white-balance button icon. However, the lamp-button icon, the pump-button icon, and the white-balance button icon need not be included in the basic command-input display. As long as the light-switching function, the pump-switching function, and the white-balance-start switching function are activated by operating the mechanical switch unit 24, the same effect as in the first and second embodiments is achieved. In addition, at least one of these functions may be carried out by operating the mechanical switch unit 24.

In the above first and second embodiments, the user's command input is recognized when the LCD is touched. However, any other input method for an LCD, such as pointing, may be adapted. There are many kinds of touch-panel monitor, such as the capacitive type, the optical-imaging type, the surface acoustic wave type, and the resistive type. The user's command input may be recognized when a behavior adequate for a selected touch-panel monitor is carried out.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2006-285052 (filed on Oct. 19, 2006), which is expressly incorporated herein, by reference, in its entirety.

The invention claimed is:

1. An endoscope processor that controls an endoscope system comprising an electronic endoscope and said endoscope processor, the electronic endoscope being configured for observing a subject, the electronic endoscope including a light source, a pump and a white balance adjustment said endoscope processor comprising:

a touch-panel input that comprises a touch-panel monitor, a command to carry out a function of said endoscope system being input via a command-input display displayed on said touch-panel monitor;

a mechanical switch which is configured to be manipulated to carry out at least one function from a light-switching function, a pump-switching function, and a white-balance-start switching function, the light source of the electronic endoscope configured to illuminate the subject being switched on or off by said light-switching function, the pump of the electronic endoscope configured to send a fluid to a peripheral area of the subject being started or stopped by said pump-switching function, and a white-balance adjustment of said the electronic endoscope starting upon activation of said white-balance-start switching function; and a controller that is configured to carry out a function corresponding to said command input via said touch-panel input or said mechanical switch, said controller comprising first and second controllers, said first controller performs said function corresponding to said command input on said mechanical switch, said second controller drives said touch-panel input and communicates said command input on said touch-panel input to said first controller, and wherein said first controller performs said function corresponding to said command input on said touch-panel input when said command input on said touch-panel input is communicated to said first controller by the second controller and said first controller, when said command input on said touch panel input is communicated from the second controller, performs said function corresponding to said command input, and when a command input communicated from the second controller is not received by said first controller, said first controller performs said function corresponding to said command input on said mechanical switch.

2. The endoscope processor according to claim 1, wherein at least one function of said light-switching function, said pump-switching function, and said white-balance-start switching function is carried out by inputting a command to said touch-panel input.

* * * * *